US007951327B2

(12) United States Patent
Reisfeld et al.

(10) Patent No.: US 7,951,327 B2
(45) Date of Patent: May 31, 2011

(54) PHOTOCATALYTIC AIR PURIFIER FOR A FAN COIL UNIT

(75) Inventors: Bradley Reisfeld, Fort Collins, CO (US); Robert Hong Leung Chiang, Shanghai (CN); Olivier Josserand, La Boisse (FR); Kevin B. Dunshee, Camillus, NY (US); Thierry Jomard, Faramans (FR); Thomas E. Drago, Liverpool, NY (US); Stephen O. Hay, Tolland, CT (US); Timothy N. Obee, South Windsor, CT (US); Joseph J. Sangiovanni, West Suffield, CT (US); Robert J. Hall, Nutley, NJ (US); Allen Murray, Bloomfield, CT (US)

(73) Assignee: Carrier Corporation, Farmington, CT (US)

( * ) Notice: Subject to any disclaimer, the term of this patent is extended or adjusted under 35 U.S.C. 154(b) by 49 days.

(21) Appl. No.: 12/512,584

(22) Filed: Jul. 30, 2009

(65) Prior Publication Data
US 2009/0288941 A1 Nov. 26, 2009

Related U.S. Application Data

(62) Division of application No. 10/700,749, filed on Nov. 4, 2003, now Pat. No. 7,758,821, which is a division of application No. 09/916,876, filed on Jul. 30, 2001, now Pat. No. 6,884,399.

(51) Int. Cl.
*B01J 19/08* (2006.01)
(52) U.S. Cl. .......................................... 422/24; 422/121
(58) Field of Classification Search .............. 422/186.3, 422/121, 24
See application file for complete search history.

(56) References Cited

U.S. PATENT DOCUMENTS

| | | | |
|---|---|---|---|
| 3,949,607 A | 4/1976 | Nodolf | |
| 4,892,712 A | 1/1990 | Robertson et al. | |
| 5,029,810 A | 7/1991 | Finnerty | |
| 5,045,288 A | 9/1991 | Raupp et al. | |
| 5,658,530 A | 8/1997 | Dunn | |
| 5,736,055 A | 4/1998 | Cooper | |
| 5,891,399 A | 4/1999 | Owesen | |
| 5,919,422 A | 7/1999 | Yamanaka et al. | |
| 5,993,738 A * | 11/1999 | Goswani | 422/22 |
| 6,063,170 A | 5/2000 | Deibert | |
| 6,063,343 A | 5/2000 | Say et al. | |

(Continued)

FOREIGN PATENT DOCUMENTS
EP 0306301 3/1989
(Continued)

*Primary Examiner* — Kishor Mayekar
(74) *Attorney, Agent, or Firm* — Marjama Muldoon Blasiak & Sullivan LLP

(57) ABSTRACT

A photocatalytic air purifier is disclosed. The photocatalytic purifier includes filter structures coated with a catalytic material such as titanium dioxide. One or more UV lamps are interposed between the filter structures. The catalytic layer reacts with airborne VOCs and bioaerosols when activated by the UV lamps to thereby oxidize the VOCs and destroy the bioaerosols. The photocatalytic air purifier does not need to be replaced or regenerated after a period of continuous usage. The photocatalytic purifier of the present invention substantially eliminates odors, VOCs, and bioaerosols from air directed through the fan coil. The photocatalytic air purifier includes a control system that optimizes operating costs. Because of these features, service, maintenance, and filter replacement are reduced to a minimum. At the same time, the well being of persons living in the space conditioned by the photocatalytic air purifier is improved.

19 Claims, 5 Drawing Sheets

U.S. PATENT DOCUMENTS

| | | | |
|---|---|---|---|
| 6,090,489 A | 7/2000 | Hayakawa et al. | |
| 6,099,798 A | 8/2000 | Kambe et al. | |
| 6,179,971 B1 | 1/2001 | Kittrell et al. | |
| 6,491,883 B2 * | 12/2002 | Mori et al. | 422/306 |
| 6,531,100 B1 * | 3/2003 | Ogata et al. | 422/177 |
| 6,589,476 B1 | 7/2003 | Fencl | |
| 6,607,702 B1 | 8/2003 | Kang et al. | |
| 2002/0005145 A1 | 1/2002 | Sherman | |
| 2002/0094298 A1 | 7/2002 | Monagan | |
| 2003/0047521 A1 | 3/2003 | McGinness | |
| 2003/0050196 A1 | 3/2003 | Hirano et al. | |
| 2003/0057404 A1 | 3/2003 | Nishii et al. | |
| 2003/0103889 A1 | 6/2003 | Mirsky et al. | |
| 2003/0104930 A1 | 6/2003 | Osawa et al. | |
| 2003/0150707 A1 | 8/2003 | Carmignani et al. | |

FOREIGN PATENT DOCUMENTS

| | | |
|---|---|---|
| EP | 0812301 | 12/1997 |
| EP | 1066878 | 1/2001 |
| EP | 1118385 | 7/2001 |
| EP | 1199103 | 4/2002 |
| EP | 1205243 | 5/2002 |
| EP | 1254870 | 11/2002 |
| EP | 1302234 | 4/2003 |
| GB | 2298149 | 8/1996 |
| GB | 2367495 | 4/2002 |
| JP | 01159033 | 6/1989 |
| JP | 01238868 | 9/1989 |
| JP | 02169040 | 6/1990 |
| JP | 07284523 | 10/1995 |
| JP | 07328351 | 12/1995 |
| JP | 08103631 | 4/1996 |
| JP | 08117560 | 5/1996 |
| JP | 08182749 | 7/1996 |
| JP | 08197046 | 8/1996 |
| JP | 08229546 | 9/1996 |
| JP | 09000940 | 1/1997 |
| JP | 09000941 | 1/1997 |
| JP | 09084866 | 3/1997 |
| JP | 09085051 | 3/1997 |
| JP | 09085052 | 3/1997 |
| JP | 09135891 | 5/1997 |
| JP | 09192496 | 7/1997 |
| JP | 09196399 | 7/1997 |
| JP | 09267043 | 10/1997 |
| JP | 09294919 | 11/1997 |
| JP | 09299754 | 11/1997 |
| JP | 10005598 | 1/1998 |
| JP | 10033653 | 2/1998 |
| JP | 10061986 | 3/1998 |
| JP | 10066879 | 3/1998 |
| JP | 10118519 | 5/1998 |
| JP | 10192654 | 7/1998 |
| JP | 10253096 | 9/1998 |
| JP | 10277366 | 10/1998 |
| JP | 10277402 | 10/1998 |
| JP | 10281484 | 10/1998 |
| JP | 10281485 | 10/1998 |
| JP | 10281486 | 10/1998 |
| JP | 10296042 | 11/1998 |
| JP | 10337442 | 12/1998 |
| JP | 11033413 | 2/1999 |
| JP | 11090176 | 4/1999 |
| JP | 11091345 | 4/1999 |
| JP | 11104225 | 4/1999 |
| JP | 11104226 | 4/1999 |
| JP | 11123316 | 5/1999 |
| JP | 11128630 | 5/1999 |
| JP | 11128750 | 5/1999 |
| JP | 11129746 | 5/1999 |
| JP | 11133017 | 5/1999 |
| JP | 11147051 | 6/1999 |
| JP | 11157332 | 6/1999 |
| JP | 11165037 | 6/1999 |
| JP | 11192942 | 7/1999 |
| JP | 11198640 | 7/1999 |
| JP | 11207149 | 8/1999 |
| JP | 11211209 | 8/1999 |
| JP | 11239717 | 9/1999 |
| JP | 11244707 | 9/1999 |
| JP | 11248239 | 9/1999 |
| JP | 11276563 | 10/1999 |
| JP | 11276564 | 10/1999 |
| JP | 11276568 | 10/1999 |
| JP | 11276903 | 10/1999 |
| JP | 11276906 | 10/1999 |
| JP | 11-314017 A * | 11/1999 |
| JP | 11314017 | 11/1999 |
| JP | 11319445 | 11/1999 |
| JP | 11348552 | 12/1999 |
| JP | 2000000293 | 1/2000 |
| JP | 2000005289 | 1/2000 |
| JP | 2000014756 | 1/2000 |
| JP | 2000015033 | 1/2000 |
| JP | 2000025450 | 1/2000 |
| JP | 2000028163 | 1/2000 |
| JP | 2000037449 | 2/2000 |
| JP | 2000042093 | 2/2000 |
| JP | 2000042364 | 2/2000 |
| JP | 2000055432 | 2/2000 |
| JP | 2000060948 | 2/2000 |
| JP | 2000070355 | 3/2000 |
| JP | 2000070671 | 3/2000 |
| JP | 2000093807 | 4/2000 |
| JP | 2000102596 | 4/2000 |
| JP | 2000107271 | 4/2000 |
| JP | 2000140087 | 5/2000 |
| JP | 2000157839 | 6/2000 |
| JP | 2000167353 | 6/2000 |
| JP | 2000171066 | 6/2000 |
| JP | 2000217902 | 8/2000 |
| JP | 2000227248 | 8/2000 |
| JP | 2000262605 | 9/2000 |
| JP | 2000262606 | 9/2000 |
| JP | 2000279494 | 10/2000 |
| JP | 2000304312 | 11/2000 |
| JP | 2000308676 | 11/2000 |
| JP | 2000320318 | 11/2000 |
| JP | 2001000814 | 1/2001 |
| JP | 2001009016 | 1/2001 |
| JP | 2001009017 | 1/2001 |
| JP | 2001029721 | 2/2001 |
| JP | 2001079069 | 3/2001 |
| JP | 2001095902 | 4/2001 |
| JP | 2001096114 | 4/2001 |
| JP | 2001104457 | 4/2001 |
| JP | 2001129364 | 5/2001 |
| JP | 2001137661 | 5/2001 |
| JP | 2001149452 | 6/2001 |
| JP | 2001149453 | 6/2001 |
| JP | 2001163032 | 6/2001 |
| JP | 2001187122 | 7/2001 |
| JP | 2001187350 | 7/2001 |
| JP | 2001190646 | 7/2001 |
| JP | 2001238940 | 9/2001 |
| JP | 2001239160 | 9/2001 |
| JP | 2001246228 | 9/2001 |
| JP | 2001293069 | 10/2001 |
| JP | 2001293078 | 10/2001 |
| JP | 2001336796 | 12/2001 |
| JP | 2002078782 | 3/2002 |
| JP | 2002263176 | 9/2002 |
| JP | 2002291852 | 10/2002 |
| JP | 2002306580 | 10/2002 |
| JP | 2002369868 | 12/2002 |
| JP | 2003004269 | 1/2003 |
| WO | WO-9740936 | 11/1997 |
| WO | WO-9919052 | 4/1999 |
| WO | WO-0119415 | 3/2001 |
| WO | WO-02102423 | 12/2002 |

* cited by examiner

PHOTOCATALYTIC AIR PURIFIER FOR A FAN COIL UNIT

CROSS REFERENCE TO RELATED APPLICATION

This is a divisional application of U.S. patent application Ser. No. 10/700,749, filed Nov. 4, 2003, now U.S. Pat. No. 7,758,821, the entirety of which is incorporated herein by reference, which is a divisional application of U.S. patent application Ser. No. 09/916,876, filed Jul. 30, 2001, now U.S. Pat. No. 6,884,399, the entirety of which is incorporated herein by reference.

FIELD OF THE INVENTION

The present invention relates generally to air purifiers, and particularly to photocatalytic purifiers.

TECHNICAL BACKGROUND

Most fan coil units consist of a water coil or a direct expansion coil, a fan, and ductwork to distribute conditioned air. Before heating or cooling, air is directed through a filter of some sort. There are various types of filters. One type of filter is referred to as a media filter. This type of filter retains dust and other particulate matter. After prolonged usage, media filters become clogged and need to be replaced.

Another type of filter currently being used is known as a HEPA filter. HEPA is an acronym for "high efficiency particulate air." HEPA filters can capture 99.9% of all particles, including sub-micron sized particles. These filters are useful in mitigating the effects of bioaerosols and dust. They are currently being used in hospitals, manufacturing clean rooms, and in other applications where clean air is considered vital. Typically, HEPA filters have an operational life span of twenty-four (24) months. After that, efficiency decreases markedly, and HEPA filters must be replaced.

Another type of filter currently being used are activated carbon adsorption filters. These filters were developed in response to industrial emissions of volatile organic compounds (VOCs). In an activated carbon adsorption system, contaminated air is directed across a bed of carbon. The carbon extracts the VOCs from the air and adsorbs the VOCs by holding them to its surface. One problem with activated carbon adsorption filters is that the air stream being filtered cannot have a high moisture content because carbon adsorbs moisture. Air having a high moisture content will quickly fill the carbon bed to capacity. Second, the air being filtered cannot include a large amount of particulate matter. The particulate matter will also clog the carbon bed. Thus, the activated carbon adsorption filter may require a pre-filter to reduce the particulate content and a dehumidifier to reduce moisture content to be effective.

An air filter is needed that substantially eliminates odors, VOCs, and bioaerosols from an air mass without requiring extensive service or maintenance. A need exists for a photocatalytic air purifier that can be conveniently installed and removed for maintenance purposes.

SUMMARY OF THE INVENTION

The present invention is directed to a photocatalytic air purifier that can be conveniently installed and removed for maintenance purposes. The photocatalytic purifier of the present invention substantially eliminates odors, VOCs, and bioaerosols from air that is directed through a duct or a fan coil. The photocatalytic air purifier of the present invention is suitable for both commercial and residential applications and can be installed in either original equipment or retrofitted into existing installations.

One aspect of the present invention is a modular photocatalytic air purifier. The photocatalytic purifier including a modular enclosure having a retractable alignment mechanism. The retractable alignment mechanism is configured to move the modular enclosure between an in-use position aligned within the fan coil unit and a retracted position. A plurality of support structures are disposed within the modular enclosure, each of the plurality of support structures having a catalytic layer disposed thereon. At least one UV lamp is interposed between the plurality of support structures.

In another aspect, the present invention includes a fan coil unit having an air return, a coil unit, a fan, and an air supply. The fan coil unit includes at least one photocatalytic purifier disposed adjacent the coil unit. The at least one photocatalytic purifier includes a modular enclosure having a retractable alignment mechanism. The retractable alignment mechanism is configured to move between an in-use position aligned within the fan coil unit and a retracted position. A plurality of support structures are disposed within the modular enclosure, each of the plurality of support structures having a catalytic layer disposed thereon, and at least one UV lamp interposed between the plurality of support structures. A control unit may be coupled to the at least one photocatalytic purifier, whereby the control unit energizes the at least one UV lamp in accordance with a fan coil operating mode.

In yet another aspect, the present invention includes a method for filtering air in a unit having an air return, and an air supply. The method includes providing at least one modular photocatalytic purifier. The at least one photocatalytic purifier includes a modular enclosure having a retractable alignment mechanism, and at least one UV lamp interposed between a plurality of titanium dioxide coated filter structures. The retractable alignment mechanism is used to dispose the at least one modular photocatalytic purifier in an in-use position within the unit. Air is directed from the air return into the at least one photocatalytic purifier. Contaminants borne by the air are brought into contact with the titanium dioxide coated filter structures. UV radiation is directed from the at least one UV lamp onto the titanium dioxide coated filter structures, whereby the titanium dioxide coated filter structures are activated to react with the contaminants to produce carbon dioxide and water.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF THE PREFERRED EMBODIMENTS

Figure 1:
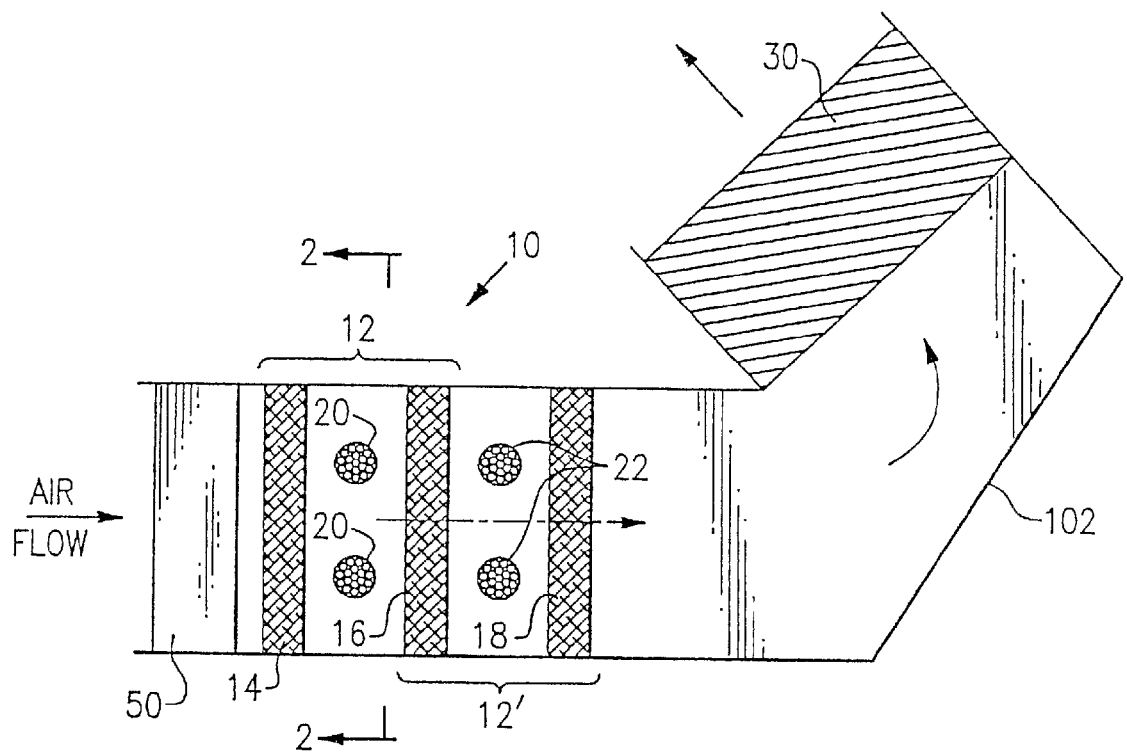
FIG. 1 is a plan view of a photocatalytic purifier in accordance with the present invention.

Reference will now be made in detail to the present preferred embodiments of the invention, examples of which are illustrated in the accompanying drawings. Wherever possible, the same reference numbers will be used throughout the drawings to refer to the same or like parts. An exemplary embodiment of the photocatalytic purifier of the present invention is shown in FIG. 1, and is designated generally throughout by reference numeral 10.

In accordance with the invention, the present invention includes a photocatalytic air purifier for use in a fan coil unit or a duct. The purifier features a modular enclosure having a retractable alignment mechanism. The retractable alignment mechanism is configured to move the enclosure between an in-use position aligned within the fan coil unit and a retracted position. The photocatalytic purifier includes a first honey-combed filter structure having a catalytic layer disposed thereon. A second honey-combed filter structure is disposed adjacent to the first honey-combed filter structure, the second honey-combed filter structure also having the catalytic layer disposed thereon. At least one UV lamp is disposed between the first honey-combed filter structure and the second honey-combed filter structure. The catalytic layer reacts with airborne VOCs and bioaerosols when activated by UV light to thereby oxidize the VOCs and destroy the bioaerosols.

Thus, the photocatalytic purifier of the present invention substantially eliminates odors, VOCs, and bioaerosols from air directed through a fan coil while reducing service and maintenance to a minimum. Further, the photocatalytic air purifier is conveniently installed and removed for maintenance purposes.

As embodied herein and depicted in FIG. 1, a plan view of a photocatalytic purifier in accordance with the present invention is disclosed. Photocatalytic purifier 10 is disposed in fan coil housing 102, between media filter 50 and fan coil unit 30. One of ordinary skill in the art will recognize that this embodiment of the present invention can also be employed in a duct system instead of a fan coil unit. Photocatalytic purifier 10 includes at least one filter layer 12 having at least one UV lamp 20 disposed between honey-combed filter element 14 and honey combed filter element 16. In the embodiment depicted in FIG. 1, a second photocatalytic purifier layer 12' is formed by disposing UV lamps 22 between filter element 16 and filter element 18. Each additional filter layer 12 increases the efficiency of filter 10. Thus, photocatalytic purifier 10 may include a plurality of filter layers 12 that include at least one UV lamp 20 disposed between honey-combed filter elements 14 and 16.

Figure 2:
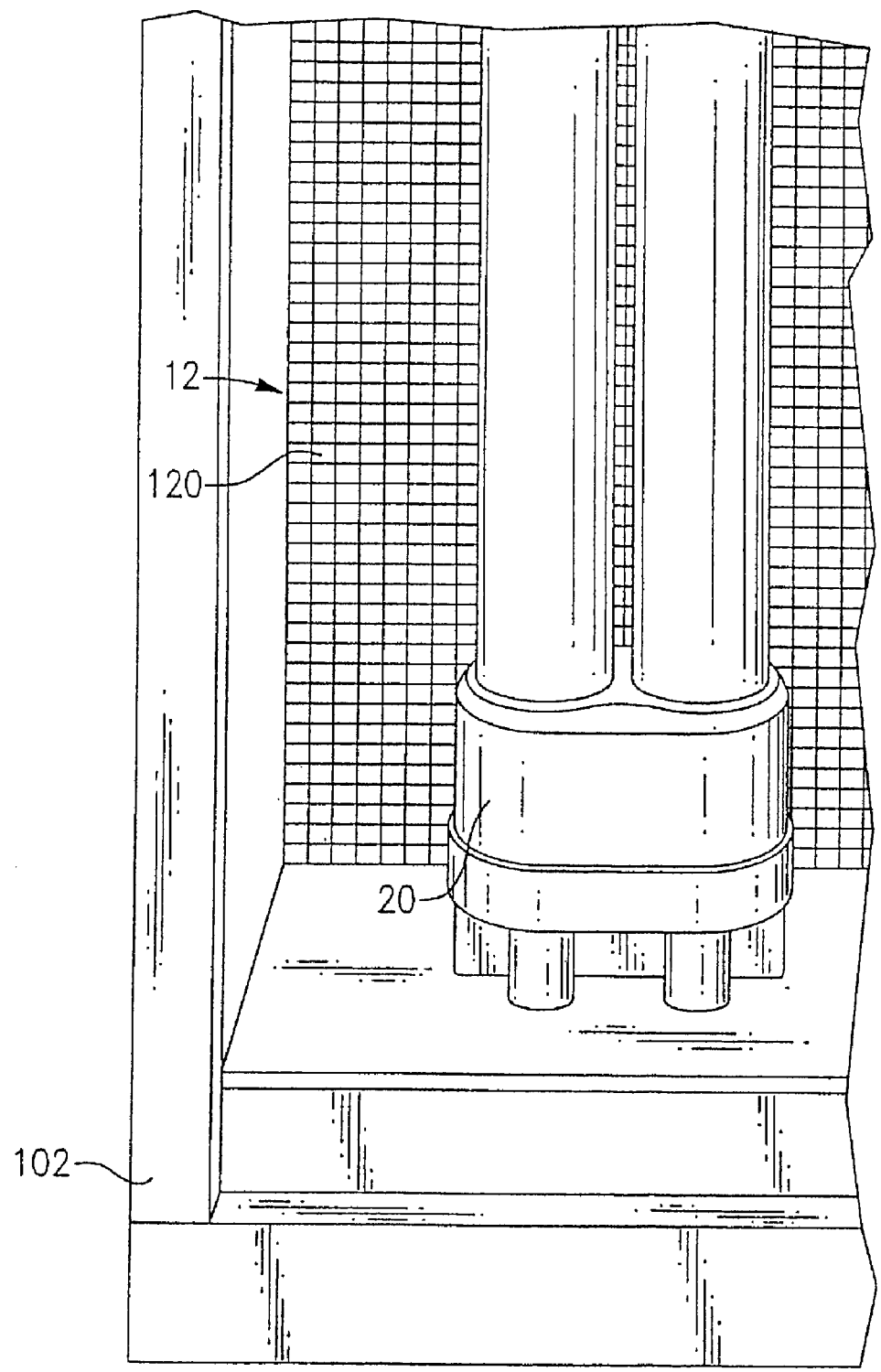
FIG. 2 is a cross-sectional view of the photocatalytic purifier taken through line A-A in FIG. 1.

FIG. 2 is a cross-sectional view of filter 10 taken through line A-A in FIG. 1. The cross-sectional view clearly shows the honey-combed structure of filter element 12. Any suitable structure may be employed, however, the honey-combed structure of filter elements 12, 14, and 16 is preferred because air pressure is maintained as air is directed through filter 10. Filter elements 12, 14, and 16 include catalytic coating 120 disposed thereon. As depicted in FIG. 2, UV lamps 20 are positioned to direct UV radiation into the interior of honey-combed filter elements 12 and 14. As shown in FIG. 2, the cross-section of photocatalytic purifier 10 is equal to the cross-section of fan coil housing 102. Thus, purifier 10 purifies the entire volume of air passing through the fan coil.

Figure 3:
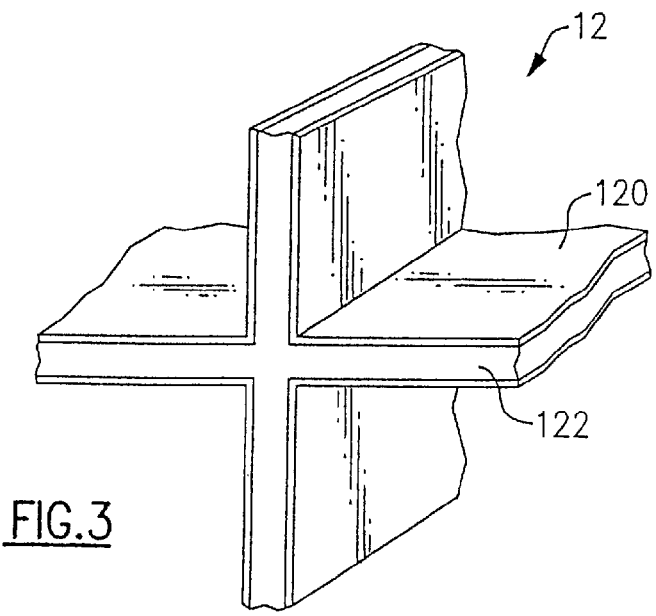
FIG. 3 is a detail view of the honey-combed filter element depicted in FIG. 2.

FIG. 3 is a detail view of honey-combed filter element 12, showing catalytic coating 120 and substrate 122. One of ordinary skill in the art will recognize that any suitable catalytic coating 120 may be disposed on elements 12, 14, or 16, but there is shown by way of example a coating of titanium dioxide. One of ordinary skill in the art will also recognize that any suitable material may be used as a substrate material for filter elements 12, 14, and 16, but there is shown by way of example a ceramic substrate. In other embodiments, an aluminum substrate or an FeCrAlY alloy substrate are used. Both the ceramic and aluminum substrates are desirable in applications requiring non-flammable filter elements. If non-flammability is not an issue, substrate 122 used in filter elements 12, 14, and 16 could be fabricated using a paper material. One of ordinary skill in the art will also recognize that any suitable substrate geometry may be used. The geometry can include honey-combs, fins, mesh, a filter-type structure, a fibrous type, or a filamentous structure.

Photocatalytic purifier 10 employs photocatalytic oxidation technology to substantially eliminate odors, VOCs, and bioaerosols. Air propagating through purifier 10 passes over catalytic layer 120. In gas-solid photocatalytic oxidation (PCO), a VOC laden air stream is brought into contact with a titania catalyst disposed on layer 120. The UV light activates the catalyst. The VOCs react with the activated catalyst and are converted into carbon dioxide and water via oxidation. This process occurs at room temperature. Since the process occurs at room temperature, the operating cost is much lower than conventional high temperature thermal oxidizers. PCO destroys a wide range of contaminants in air streams. Filter elements 14, 16, and 18 are not degraded over time by UV light and thus, they do not need to be replaced even after continuous prolonged usage. It should also be mentioned that bioaerosols are also destroyed by their exposure to UV light.

Figure 4:
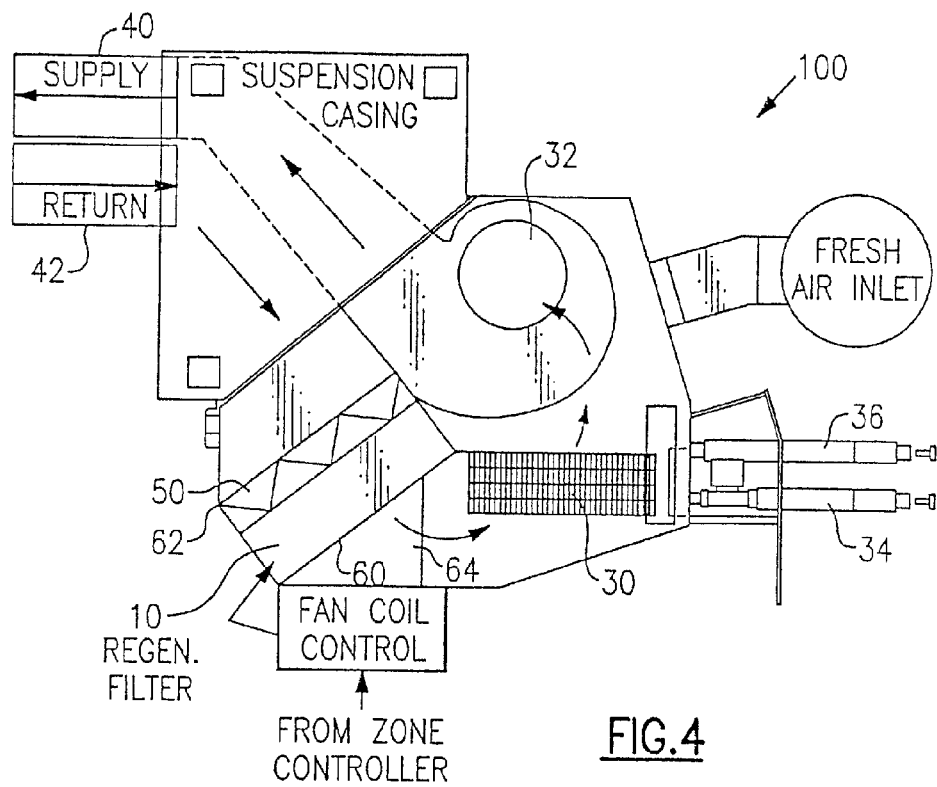
FIG. 4 is a diagrammatic depiction of a fan coil unit in accordance with a first embodiment of the invention showing the photocatalytic purifier depicted in FIGS. 1-3 in an in-use position.
Figure 5:
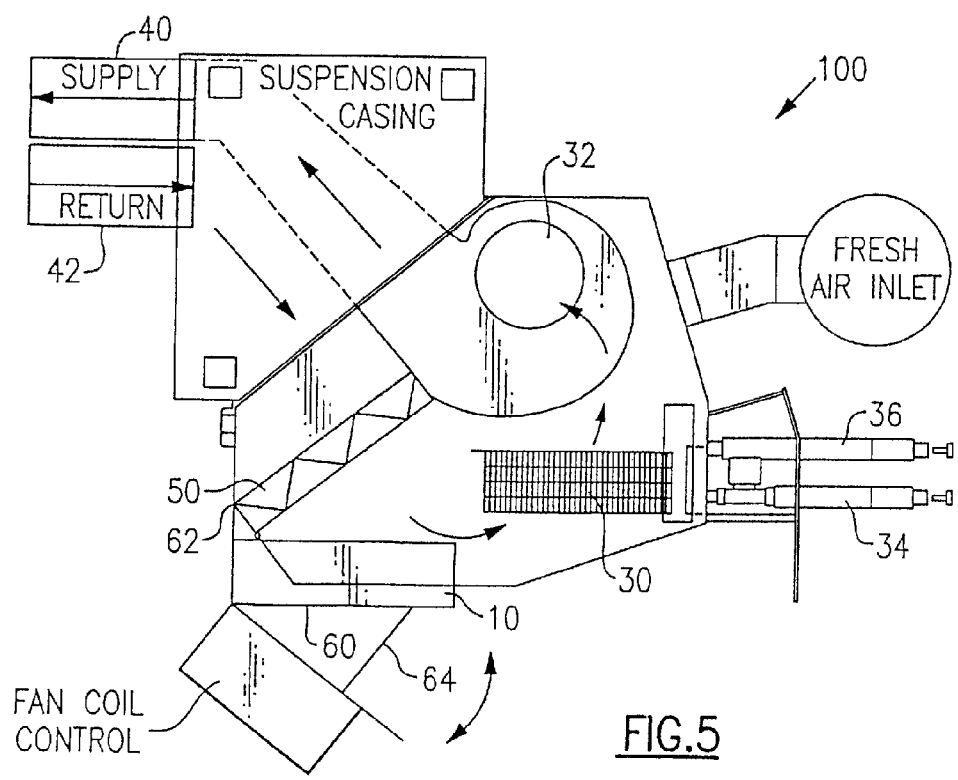
FIG. 5 is a diagrammatic depiction of a fan coil unit in accordance with the first embodiment of the invention showing the photocatalytic purifier depicted in FIGS. 1-3 in a retracted position.

As embodied herein, and depicted in FIG. 4, fan coil unit 100 includes housing 102 which is connected to suspension casing 104. Suspension casing 104 is attached to a ceiling or some other structural element of the building accommodating fan coil unit 100. Fan coil unit 100 includes photocatalytic purifier 10 which is disposed in housing 102 between media filter 50 and fan coil 30. Fan coil 30 includes cold water supply 34 and hot water supply 36. Both cold water supply 34 and hot water supply 36 include valves (not shown) that are controlled by fan coil controller 110 to thereby regulate heating and cooling within the conditioned space. Fan coil unit 100 also includes fan 32 which draws an air stream from air return 42 through photocatalytic purifier 10 and fan coil 30. The air stream is then directed into the conditioned space via air supply duct 40. In FIG. 4, photocatalytic purifier 10 is shown in the in-use position, being disposed adjacent to filter 50. Photocatalytic purifier 10 includes modular enclosure 60 having a retractable alignment mechanism 62. Retractable alignment mechanism 62 is configured to move enclosure 60 between an in-use position aligned within the fan coil unit, and a retracted position. In this embodiment, alignment mechanism 62 is a hinged door structure. Mechanism 62 includes arm 64 that is used to hold enclosure 60 in the in-use position. The retracted position is depicted in FIG. 5.

An alternative embodiment is a sliding arrangement wherein the photocatalytic purifier 10 can be made to slide from its installed position to a retracted position as shown by the dashed lines in FIG. 4.

It will be apparent to those of ordinary skill in the pertinent art that modifications and variations can be made to fan coil control 110 of the present invention depending on cost requirements and the complexity of the application. For example, fan coil unit 100 can be deployed as a stand-alone unit in a single family dwelling, or as one unit among many in a complex architecture. For example, fan coil unit 100 may be employed in a multi-storied structure having a plurality of air-conditioned zones. Fan coil control 110 includes firmware containing the control program necessary to control the water valves, fan 32, and UV lamps 20, 22, and 24 included in photocatalytic purifier 10. The control program is executed by an embedded microprocessor included in fan coil control 110. In another embodiment, fan coil control 110 is implemented using a logic controller.

Fan coil control 110 includes several operational modes 80 that are selected by a switch 81. The first mode is an "unoccupied mode." In this mode, the level of comfort provided by fan coil unit 100 does not have to be at an optimum level because no one is in the conditioned space as determined by the sensor 82. The heating and cooling of the air conditioned zone is regulated in accordance with a wider "dead-band." Thus, controller 110 allows the ambient air temperature of the air conditioned zone to vary within a wide range temperatures before providing either heating or cooling. The UV lamps are generally inoperative during this mode but may be on for some lead/lay time before or after occupancy.

The second mode is referred to as the "occupied mode." In this mode, the level of comfort provided by fan coil unit 100 is optimized because of the presence of people in the conditioned space. Thus, the UV lamps are always operating in this mode. The occupied mode includes a "demand" sub-mode wherein fan 32 is operating at a higher speed, and a "satisfied" sub-mode wherein fan 32 is operative at a lower speed. In other embodiments, controller 110 uses a "tolerance index" as a control metric. Controller 110 may include a motion detector input to determine whether the conditioned space is occupied.

A third mode is provided by controller 110. It is known as the "frost protection mode." The frost protection mode initiates heating within a conditioned space only to maintain a minimum air temperature within the air conditioned space. Since the air conditioned space is assumed to be unoccupied, the UV lamps are not operative in this mode. In addition to temperature sensors 86, controller 110 may include a sensor 87 input coupled to window contacts, enabling it to recognize an open window condition. In another embodiment, the frost protection mode initiates heating during the open window condition. An indoor air quality (IAQ) sensor 88 provides feedback to the fan coil control 110 as to the quality of air in the particular zone being conditioned.

As embodied herein and depicted in FIG. 5, a diagrammatic depiction of fan coil unit 100 showing photocatalytic purifier 10 in a retracted position is disclosed. In the retracted position, hinged door structure 62 retracts to provide access to purifier 10 during maintenance or the removal of purifier 10. Arm 64 is detached from purifier 10 during removal.

Figure 6:
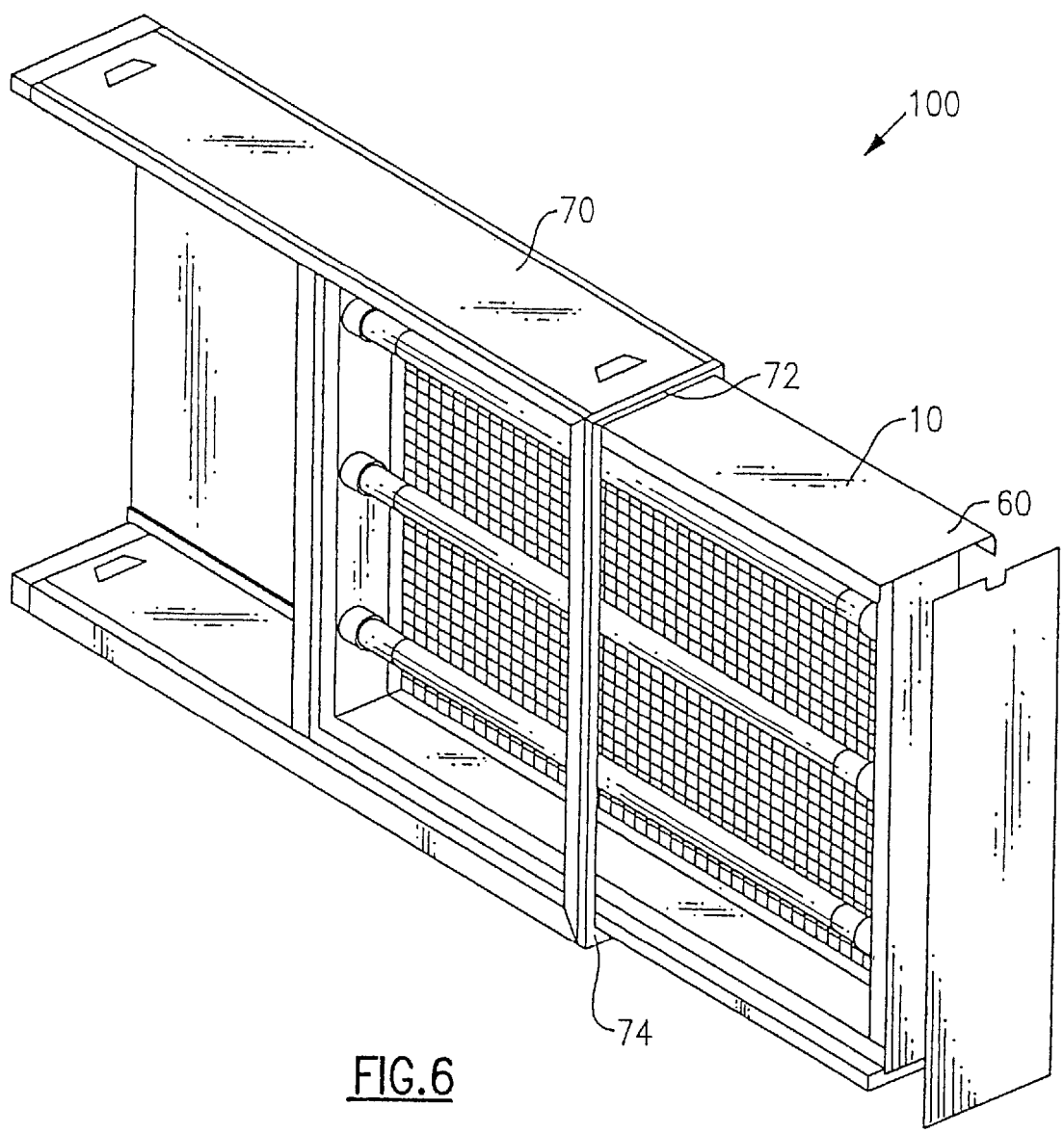
FIG. 6 is a diagrammatic depiction of a fan coil unit in accordance with a second embodiment of the invention showing the photocatalytic purifier depicted in FIGS. 1-3 in a retracted position.
Figure 7:
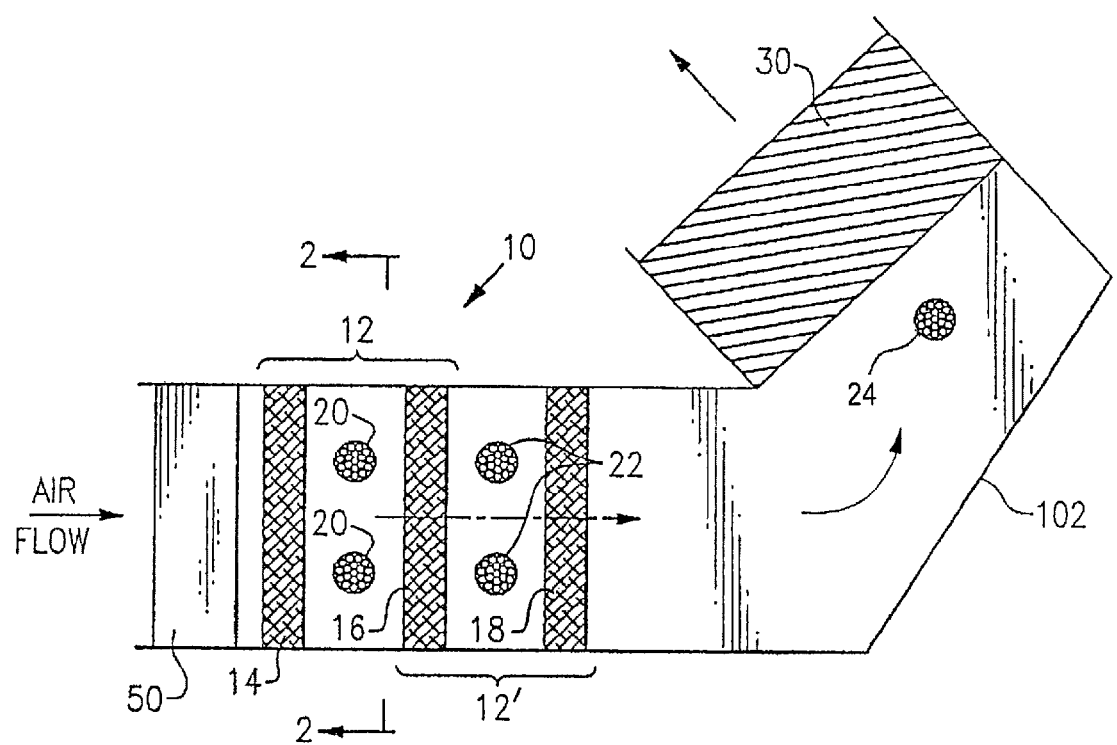
FIG. 7 is a plan view of a photocatalytic purifier in accordance with one embodiment of the invention.

As embodied herein and depicted in FIG. 6, a diagrammatic depiction of photocatalytic purifier unit 100 in accordance with a second embodiment of the invention is disclosed. In this embodiment, unit 100 is disposed in media cabinet 70. The enclosure 60 of photocatalytic purifier 10 is shown in a retracted position. Enclosure 60 is equipped with slider mechanism 72 on a top portion of enclosure 60, and is equipped with slider mechanism 74 on a bottom portion of enclosure 60. One of ordinary skill in the art will recognize that unit 100 can be a fan coil unit or part of a duct system.

It will be apparent to those skilled in the art that various modifications and variations can be made to the present invention without departing from the spirit and scope of the invention. Thus, it is intended that the present invention covers the modifications and variations of this invention provided they come within the scope of the appended claims and their equivalents.

We claim:

1. A method for filtering air in a fan coil unit having an air return, and an air supply, the method comprising:
   providing at least one modular photocatalytic purifier, the at least one photocatalytic purifier including a modular enclosure having a retractable alignment mechanism, and at least one UV lamp interposed between a plurality of titanium dioxide coated filter structures;
   using the retractable alignment mechanism to dispose the at least one modular photocatalytic purifier in an in-use position within the fan coil unit;
   directing air from the air return into the at least one photocatalytic purifier;
   bringing contaminants borne by the air into contact with the titanium dioxide coated filter structures; and
   directing UV radiation from the at least one UV lamp onto the titanium dioxide coated filter structures, wherein the titanium dioxide coated filter structures are activated to react with the contaminants to produce carbon dioxide and water.

2. The method of claim 1, wherein the step of directing UV radiation includes destroying bioaerosols in contact with the filter structures.

3. The method of claim 1, wherein the step of directing UV radiation from the at least one UV lamp includes oxidizing organic chemical compounds in contact with the filter structures.

4. The method of claim 3, further comprising:
   providing a second UV lamp disposed between the photocatalytic purifier and a fan coil;
   and directing UV radiation from the second UV lamp onto the fan coil unit.

5. The method of claim 4, wherein the step of directing UV radiation from the second UV lamp includes substantially neutralizing microbes developing on the fan coil unit.

6. The method of claim 1, further comprising:
   providing a media filtration filter disposed between the air return and the photocatalytic purifier; and
   trapping airborne particulate matter in the media filtration filter during the step of directing air from the air return path.

7. The method of claim 2, wherein the step of directing radiation includes selectively energizing the at least one UV lamp in accordance with an operational mode of a fan coil unit.

8. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a non-flammable substrate.

9. The method of claim 1, wherein providing at least one modular photocatalytic purifier including at least one UV lamp interposed between a plurality of titanium dioxide coated filter structures comprises at least one modular photocatalytic purifier including at least one UV lamp interposed between a plurality of titanium dioxide coated filter structures having a ceramic substrate.

10. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a ceramic fiber substrate.

11. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having an aluminum substrate.

12. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a honey-comb structure.

13. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a fin structure.

14. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a mesh structure.

15. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures.

16. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a fibrous structure.

17. The method of claim 1, wherein providing at least one modular photocatalytic purifier including at least one UV lamp interposed between a plurality of titanium dioxide coated filter structures comprises providing at least one modular photocatalytic purifier including at least one UV lamp interposed between a plurality of titanium dioxide coated filter structures having a filamentous structure.

18. A method for purifying air comprising:
   receiving an air stream from a source;
   photocatalytically oxidizing said air stream to produce a photocatalytically oxidized air stream;
   transferring heat from said photocatalytically oxidized air stream to produce a heat transferred air stream;
   mixing fresh air with said heat transferred air stream to produce a mixed air stream; and
   delivering said mixed air stream.

19. A method for filtering air in a unit having an air return, and an air supply, the method comprising:
   providing at least one modular photocatalytic purifier, the at least one photocatalytic purifier including a modular enclosure having a retractable alignment mechanism, and at least one UV lamp interposed between a plurality of titanium dioxide coated filter structures;
   using the retractable alignment mechanism to dispose the at least one modular photocatalytic purifier in an in-use position within the unit;
   directing air from the air return into the at least one photocatalytic purifier;
   bringing contaminants borne by the air into contact with the titanium dioxide coated filter structures; and
   directing UV radiation from the at least one UV lamp onto the titanium dioxide coated filter structures, wherein the titanium dioxide coated filter structures are activated to react with the contaminants to produce carbon dioxide and water;
   providing a second UV lamp disposed between the photocatalytic purifier and a fan coil; and
   directing UV radiation from the second UV lamp onto the fan coil unit.

* * * * *